(12) United States Patent
Sun et al.

(10) Patent No.: US 9,670,115 B2
(45) Date of Patent: Jun. 6, 2017

(54) METHOD AND SYSTEM FOR PURIFYING AN ETHYLENE-CONTAINING GAS STREAM

(75) Inventors: Mingyong Sun, Louisville, KY (US); Steven A. Blankenship, Radcliff, KY (US); Michael A. Urbancic, Louisville, KY (US); Richard Paul Zoldak, Louisville, KY (US)

(73) Assignee: Clariant Corporation, Louisville, KY (US)

( * ) Notice: Subject to any disclaimer, the term of this patent is extended or adjusted under 35 U.S.C. 154(b) by 701 days.

(21) Appl. No.: 13/396,714

(22) Filed: Feb. 15, 2012

(65) Prior Publication Data

US 2013/0211162 A1   Aug. 15, 2013

(51) Int. Cl.
| | | |
|---|---|---|
| C07C 7/167 | (2006.01) | |
| C07C 7/163 | (2006.01) | |
| B01J 23/50 | (2006.01) | |
| C07C 7/148 | (2006.01) | |
| B01J 35/00 | (2006.01) | |
| B01J 23/46 | (2006.01) | |
| B01J 35/10 | (2006.01) | |
| B01J 37/02 | (2006.01) | |
| C10G 70/00 | (2006.01) | |
| C10G 70/02 | (2006.01) | |

(52) U.S. Cl.
CPC ............ *C07C 7/167* (2013.01); *B01J 23/462* (2013.01); *B01J 23/50* (2013.01); *B01J 35/0006* (2013.01); *B01J 35/1009* (2013.01); *B01J 35/1019* (2013.01); *B01J 35/1038* (2013.01); *B01J 35/1042* (2013.01); *B01J 37/0201* (2013.01); *C07C 7/14841* (2013.01); *C10G 70/00* (2013.01); *C10G 70/02* (2013.01); *Y02P 20/52* (2015.11)

(58) Field of Classification Search
USPC ........................................... 585/262
See application file for complete search history.

(56) References Cited

U.S. PATENT DOCUMENTS

| | | | |
|---|---|---|---|
| 4,034,062 A |  7/1977 | Krueger | |
| 4,299,800 A * | 11/1981 | Nishikawa et al. | .......... 423/219 |
| 4,705,906 A | 11/1987 | Brophy et al. | |
| 6,204,218 B1 |  3/2001 | Flick et al. | |

(Continued)

FOREIGN PATENT DOCUMENTS

WO      2009031756      3/2009

OTHER PUBLICATIONS

PCT/US2013/022363 International Search Report and Written Opinion of the International Searching Authority with Mail Date of Jun. 24, 2013.

*Primary Examiner* — In Suk Bullock
*Assistant Examiner* — Philip Louie

(57) ABSTRACT

A two catalyst system is described having separate catalyst beds for the selective conversion of acetylene to ethylene which reduces the concentration of acetylene, dienes, O2, and NOx is disclosed. An ethylene containing gas stream, such as an off-gas stream from a refinery catalytic cracking unit used in the production of fuels and gas oils, is treated by first contacting the gas stream with a silver catalyst supported on a metal oxide and subsequently contacting the gas stream with a ruthenium catalyst supported on metal oxide. The two catalysts are contained within contiguous continuous reactors or reactor compartments.

11 Claims, 2 Drawing Sheets

(56) References Cited

U.S. PATENT DOCUMENTS

| | | |
|---|---|---|
| 7,220,700 B2 | 5/2007 | Lowe et al. |
| 7,301,062 B2 | 11/2007 | Gartside et al. |
| 7,357,902 B2 | 4/2008 | Hague et al. |
| 2005/0203320 A1* | 9/2005 | Ryu .............................. 585/261 |
| 2006/0166816 A1 | 7/2006 | Zhang et al. |
| 2010/0000911 A1 | 1/2010 | Rudolf et al. |
| 2010/0048972 A1* | 2/2010 | Sun et al. ..................... 585/820 |

* cited by examiner

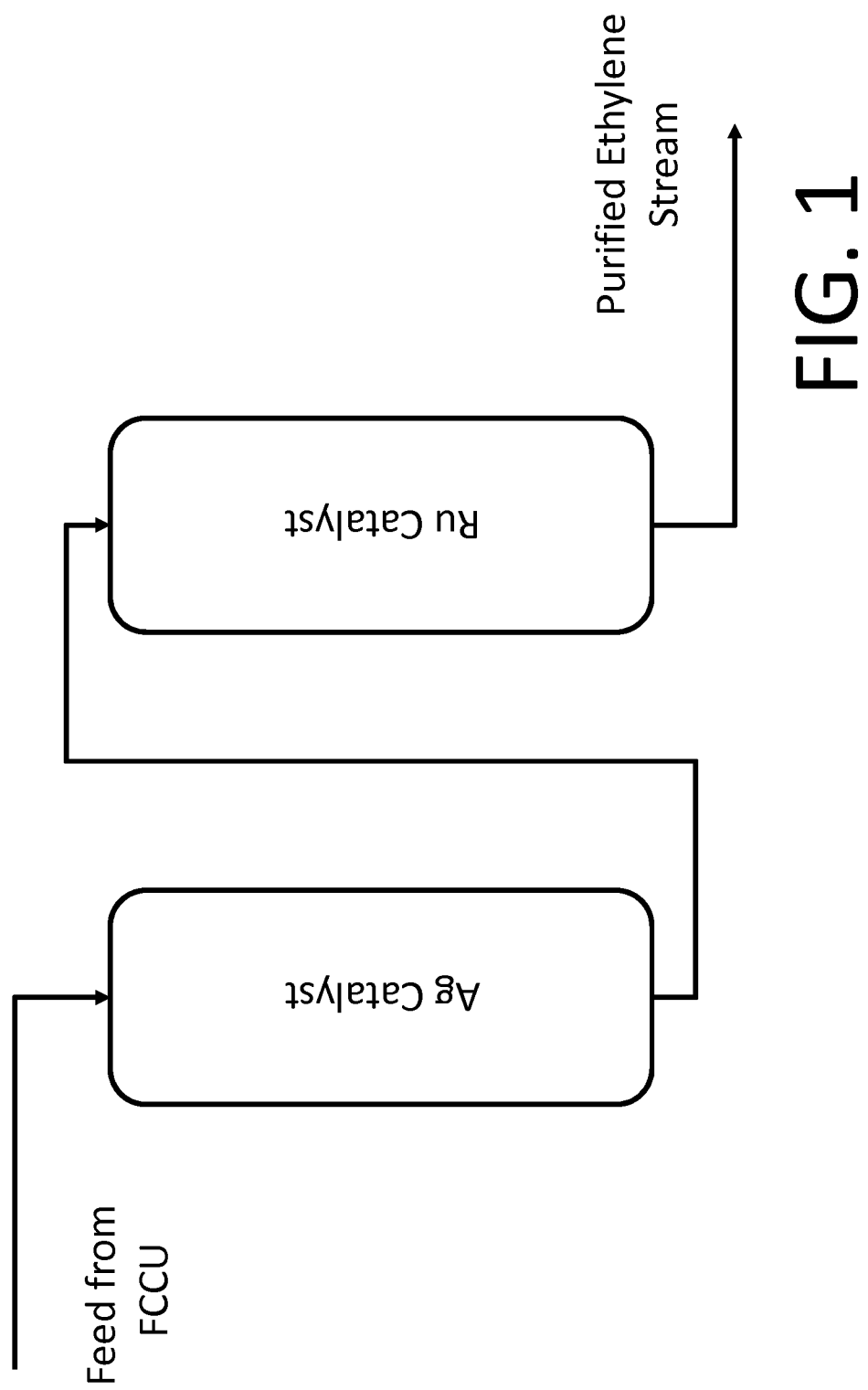

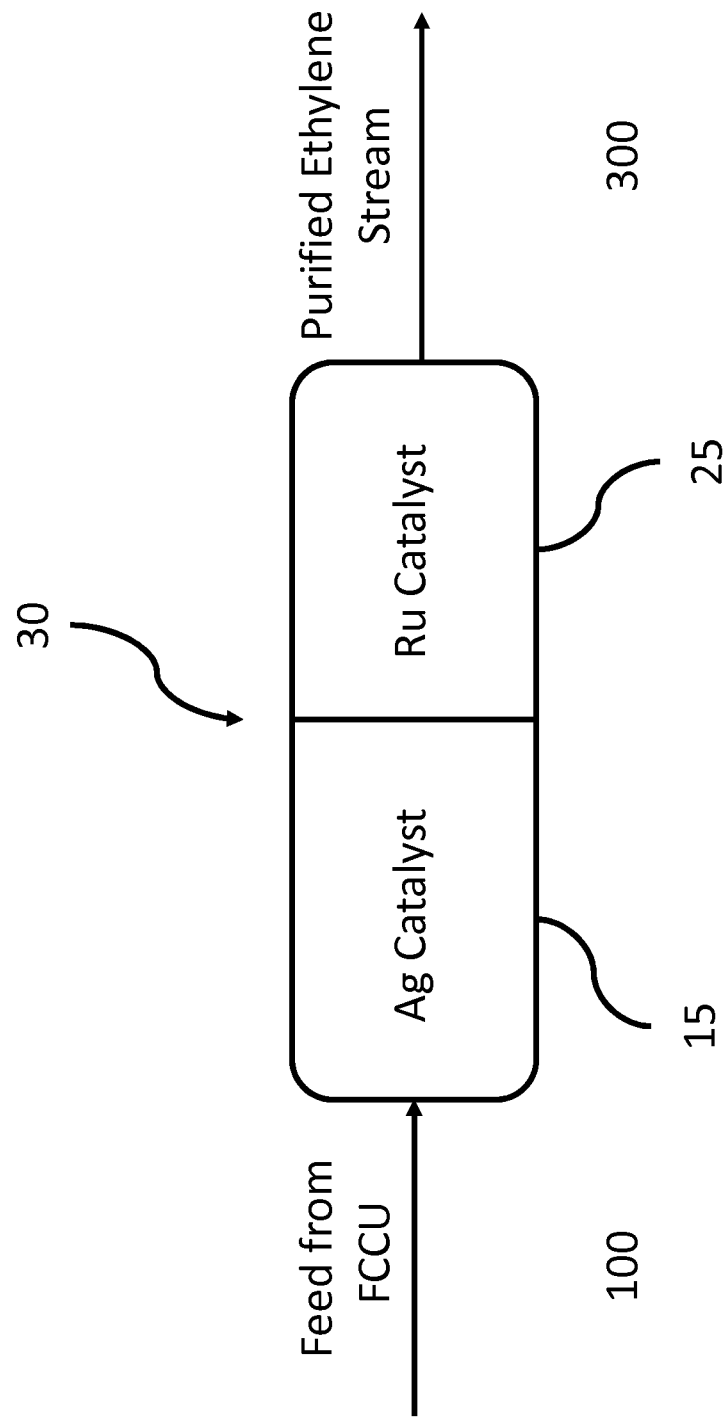

METHOD AND SYSTEM FOR PURIFYING AN ETHYLENE-CONTAINING GAS STREAM

FIELD

This system relates to the catalytic treatment of gas streams. More specifically, this system relates to the catalyzed purification of ethylene containing gas streams.

BACKGROUND

Ethylene is one of the most widely produced petrochemicals in the world. Most ethylene is produced through the cracking of hydrocarbons. Acetylene is a byproduct of ethylene production processes and acts as a poison to the catalysts used for making polyethylene out of the ethylene product. In addition, acetylene can form metal acetylides, which are explosive contaminants. Polymer-grade ethylene product should contain no more than 1 ppm of acetylene. Trace acetylene removal by selective hydrogenation is practiced commercially but is a significant challenge to the ethylene producer and catalyst manufacturer. This is due to the low acetylene concentration in the reactor effluent and the necessity to convert nearly 100% of the acetylene without decreasing ethylene yields due to the conversion of ethylene to ethane. Ethylene is a valuable feedstock for several chemical processes and it is advantageous to selectively reduce acetylene to ethylene. In the reduction of acetylene, ethylene selectivity and the useful life of the catalyst are important variables when choosing a catalyst.

Alkynes are easily chemically reduced to alkanes by the addition of $H_2$ over a metal catalyst. The reaction takes place in steps through an alkene intermediate. It is possible to selectively terminate the chemical reduction of acetylene at ethylene, prior to further chemical reduction to ethane, by controlling the selectivity of the catalyst. $Al_2O_3$ is often used as a support for metal catalysts and possesses the ability to function both as a Lewis acid and as a Lewis base. Ruthenium, while possessing the greatest activity of the platinum group metals, does have drawbacks when used as a supported metal catalyst in hydrocarbon gas streams containing acetylene.

Platinum group metals, e.g. Ruthenium, used in catalysts intended for the reduction of acetylene can convert significant fractions of acetylene into ethane through hydrogenation of ethylene.

In addition to hydrocarbons, an off-gas stream often contains nitric oxides, oxygen, sulfur, and other impurities. Most selective acetylene hydrogenation operations at the commercial scale use Pd-based catalysts. The Pd-based catalysts have high activity and selectivity for selective hydrogenation of acetylene and dienes; but they are very sensitive to sulfur and some other catalyst poisons. Moreover, the Pd-based catalysts are not known to be particularly effective for removal of nitric oxides and oxygen.

Nickel catalysts have also been used in selective hydrogenation of acetylene and dienes. Nickel catalysts are resistant to sulfur poisoning, but are not selective toward hydrogenation of acetylene. Most commonly, while acetylene is removed, significant amounts of olefins are also hydrogenated to saturated hydrocarbons. Nickel-based catalysts also tend to form nickel carbonyl when the carbon monoxide level is high in the feed gas stream, particularly at low temperatures. Nickel carbonyl is a highly volatile, highly toxic substance which can deposit in downstream equipment and pose a significant safety hazard to workers.

SUMMARY

A two catalyst system having separate catalyst beds for the selective conversion of acetylene to ethylene which reduces the concentration of acetylene, dienes, $O_2$, and $NO_x$ is disclosed. An ethylene containing gas stream, such as an off-gas stream from a refinery catalytic cracking unit used in the production of fuels and gas oils, is treated by first contacting the gas stream with a silver catalyst supported on a metal oxide and subsequently contacting the gas stream with a ruthenium catalyst supported on metal oxide. The two catalysts are contained within contiguous continuous reactors or reactor compartments.

Contacting the gas stream with a silver catalyst prior to contacting the gas stream with a ruthenium catalyst optimizes ethylene selectivity through an increase in the conversion of acetylene to ethylene with minimal conversion of ethylene to ethane. In addition, $NO_x$, $O_2$, methylacetylene, and dienes are also removed by the process.

BRIEF DESCRIPTION OF THE DRAWINGS

FIG. 1 depicts a flow diagram of a double reactor configuration having separate silver and ruthenium reactors.

FIG. 2 depicts a flow diagram of a single reactor configuration having separate silver and ruthenium reactor compartments within the single reactor.

DETAILED DESCRIPTION OF THE PREFERRED EMBODIMENTS

The present development is a method and system that can be useful in purification of raw gas or off-gas streams from catalytic crackers. By the method of the present development, acetylene, methylacetylene, dienes, NOx, and $O_2$ are simultaneously removed from a raw gas feed-stream that comprises ethylene, hydrogen, and CO without significant loss of ethylene, by contacting an ethylene containing hydrocarbon gas stream first with a supported Ag-based catalyst and subsequently with a Ru-based catalyst. The Ag-based catalyst has a Ag content of between about 0.5% by mass to about 10% by mass and the Ru-based catalyst has a Ru content of between 0.01% by mass to about 5% by mass and more preferably between 0.01% by mass to 1% by mass. The support for each metal catalyst is a metal oxide selected from $Al_2O_3$, $SiO_2$, alumino-silicates, $TiO_2$, $ZrO_2$, ZnO, MgO, $Fe_2O_3$ and $CeO_2$ or mixtures thereof, but is preferably $Al_2O_3$. The catalysts are prepared by metal impregnation/deposition methods known to those skilled in the art. Generally, the preferred catalysts have a BET surface area of from 3 $m^2/g$ to 200 $m^2/g$ and a Hg intrusion pore volume of 0.2 ml/g to 0.8 ml/g.

As depicted in FIG. 1, a two reactor configuration allows the ethylene-containing feed stream 100, e.g. olefin gas stream from an FCCU, to flow through the Ag catalyst bed reactor 10 to produce a first processed ethylene-containing gas stream 200. The first processed ethylene-containing gas stream 200 is subsequently fed to a Ru catalyst bed reactor 20 to produce a second processed ethylene-containing gas stream 300 that has been purified by the removal of impurities, i.e. acetylene, methylacetylene, dienes, NOx, and $O_2$. Alternatively, a single reactor 30 can utilize a Ag catalyst bed compartment 15 and a Ru catalyst bed compartment 25 arranged to receive an ethylene-containing gas stream 100 and produce a first processed ethylene-containing gas stream 200 from the Ag catalyst bed within the reactor 30 and subsequently flow into a Ru catalyst bed compartment 25 contained therein to produce a second processed ethylene-containing gas stream 300.

Catalysts with varying Ag and Ru concentrations were tested individually and combined into a contiguous catalyst bed in a continuous flow reactor by loading approximately 100 cc of catalyst into a reactor and then feeding a contaminated ethylene-containing feed-stream through the loaded catalyst. For testing purposes, in general, the reactor temperature is adjusted to a temperature of from about 120° C. to about 300° C., the carbon monoxide content is held between about 0.05 mol % and 5 mol %, and the sulfur content is held below about 20 ppm. The reactor pressure is held between 0.5 MPa and 5 MPa and the hydrogen partial pressure is held between about 0.05 MPa and 2 MPa with a gas hourly space velocity (GHSV) of 500 $hr^{-1}$ to 10,000 $hr^{-1}$. More preferably, the GHSV is held between 1000 $hr^{-1}$ to 5,000 $hr^{-1}$; and most preferably, the hydrogen partial pressure is held between about 0.10 MPa and 1.0 MPa with a GHSV of from about 1000 $hr^{-1}$ to 3500 $hr^{-1}$ and the feed-stream hydrogen concentration range is 5 mol % to 25 mol %.

The catalyst is reduced after being loaded into the reactor and before introduction of the ethylene-containing gas stream by feeding hydrogen or a hydrogen-containing gas through the catalyst at a temperature in excess of 100° C. for a period of time sufficient to reduce the catalysts. Six catalysts were prepared and utilized in the following examples to collect data across a variety of operating conditions and are summarized in Table 1.

EXAMPLES

TABLE 1

| Catalysts Utilized in Examples | |
|---|---|
| Catalyst 1 | 0.15% Ru on $Al_2O_3$ |
| Catalyst 2 | 0.3% Ru on $Al_2O_3$ |
| Catalyst 3 | 1% Ag on $Al_2O_3$ |
| Catalyst 4 | 3% Ag on $Al_2O_3$ |
| Catalyst 5 | 6% Ag on $Al_2O_3$ |
| Catalyst 6 | 3% Ag + 0.3% Ru on $Al_2O_3$ |

Catalysts 1-6 were tested in a continuous flow reactor. In some of the following examples a Ag catalyst was loaded in front of a Ru catalyst in a contiguous bed within the same reactor. Approximately 100 cc of catalyst is loaded into the reactor. The catalysts were pre-reduced with hydrogen at 204° C. in-situ for 3 hours before test feed mixture was introduced into the reactor. The reactor temperature is adjusted to a predetermined temperature and an ethylene-containing feed gas contaminated with $O_2$, $NO_x$, CO, acetylene, methylacetylene, and propadiene is fed through the reactor. Three different reactor feeds were prepared and then processed in the reactor using various catalysts and operating conditions. The ethylene-containing feed compositions are detailed in Table 2. Results were examined for the effectiveness of the catalyst and operating conditions at removing the feed impurities while limiting the production of ethane.

TABLE 2

| Feed Analysis | | | |
|---|---|---|---|
| Component (mol %) | Feed A | Feed B | Feed C |
| $H_2$ | 17 | 21 | 20 |
| $O_2$ | 0.08 | 0.154 | 0.25 |
| $NO_x$ |  | 0.0077 | 2 ppm |
| CO | 0.26 | 0.25 | 0.2 |
| $C_2H_6$ | 0.021 | 0.02 | 0.02 |
| $C_2H_4$ | 44.7 | 45 | 45 |
| $C_2H_2$ | 0.137 | 0.16 | 0.16 |
| $C_3H_8$ | 0.022 | 0.02 | 0.02 |
| $C_3H_6$ | 6.83 | 6.2 | 6 |
| Propadiene (PD) | 0.038 | 0.02 | 0.02 |
| Methylacetylene (MA) | 0.022 | 0.025 | 0.025 |

Example 1

Ru Catalysts

Catalyst 1 contains 0.15% Ru on $Al_2O_3$, and Catalyst 2 contains 0.3% Ru on $Al_2O_3$. Both were prepared as described in US Pub. 2010/0048972 A1. Both catalysts were tested with feed composition A, described in Table 2, at 1.75 MPa. The gas hourly space velocity (GHSV) was 1500 $h^{-1}$. The results and operating parameters are detailed in Table 3.

TABLE 3

| Ru Catalysts | | | | |
|---|---|---|---|---|
| Parameter | Catalyst 1 | | Catalyst 2 | |
| HOS | 24 | 26 | 25 | 27 |
| Avg. Bed Temp., ° C. | 173 | 178 | 133 | 124 |
| $O_2$, ppm | 3.0 | 0.87 | 0.18 | 1.65 |
| $C_2H_6$, mol % | 1.02 | 1.11 | 1.24 | 0.88 |
| $C_2H_4$, mol % | 47.1 | 46.4 | 46.6 | 46.3 |
| $C_2H_2$, mol % | 0.003 | <0.0001 | <0.0001 | 0.0037 |
| $C_3H_8$, mol % | 0.047 | 0.050 | 0.067 | 0.051 |
| $C_3H_6$, mol % | 7.3 | 7.1 | 7.8 | 7.64 |
| Propadiene, mol % | 0.035 | 0.033 | 0.021 | 0.026 |
| Methylacetylene, mol % | 0.002 | 0.002 | <0.0001 | 0.002 |

The results in Table 3 include the reactor outlet gas analytical results at different bed temperatures as well as the hours on steam. Catalyst 1 required an average bed temperature of 178° C. to reduce oxygen and acetylene to below 1 ppm, i.e. clean-up conditions. Catalyst 2 achieved clean-up conditions at an average bed temperature of 133° C. However, Catalyst 2 exhibited decreased selectivity and produced more $C_2H_6$ than Catalyst 1 at clean-up conditions.

Example 2

Ag Catalysts

Catalyst 3 contains 1% Ag loaded on $Al_2O_3$, Catalyst 4 contains 3% Ag loaded on $Al_2O_3$, and Catalyst 5 contains 6% Ag on $Al_2O_3$, which were made by normal impregnation methods. The feed composition and test conditions are substantially identical to those used in Example 1.

TABLE 4

Ag Catalysts

| Parameter | Catalyst 5 6% Ag | | Catalyst 4 3% Ag | | Catalyst 3 1% Ag | |
|---|---|---|---|---|---|---|
| HOS | 8 | 10.2 | 20 | 24.5 | 20 | 23.5 |
| Avg. Bed Temp., °C. | 130.6 | 146.7 | 126.1 | 177.2 | 125.5 | 176.7 |
| $O_2$, ppm Out | 0.44 | 0.16 | 0.17 | 0.063 | 0.26 | 0.062 |
| $C_2H_6$, mol % | 0.052 | 0.142 | 0.046 | 0.636 | 0.041 | 0.607 |
| $C_2H_4$, mol % | 56.3 | 54.2 | 53.1 | 47.8 | 48.4 | 44 |
| $C_2H_2$, mol % | 0.031 | 0.000 | 0.112 | 0 | 0.117 | 0.005 |
| $C_3H_8$, mol % | 0.02 | 0.02 | 0.021 | 0.034 | 0.018 | 0.029 |
| $C_3H_6$, mol % | 6 | 5.6 | 6.2 | 5.8 | 5.8 | 5.6 |
| Propadiene, mol % | 0.004 | 0.000 | 0.019 | 0.000 | 0.016 | 0.003 |
| Methylacetylene, mol % | 0.025 | 0.003 | 0.037 | 0.002 | 0.027 | 0.003 |

As shown in Table 4, which includes the reactor outlet gas analytical results at different bed temperatures, Catalyst 5 reduced oxygen and acetylene to clean-up conditions at 147° C. Catalyst 4 achieved clean-up conditions at 177° C. Catalyst 3 could not reduce acetylene below 1 ppm at temperatures up to 177° C.

Example 3

Ag Promoted Ru Catalysts

Catalyst 6, a Ag promoted Ru catalyst, was prepared by impregnating/depositing 3% Ag onto Catalyst 2 by normal impregnation methods known to those skilled in the art. The test conditions and feed are the same as that used in Example 1. The Ag promoted Ru catalyst could not reduce oxygen to below 1 ppm at 50° C. higher temperature than the Ru only catalyst. The results and operating parameters are detailed in Table 5.

TABLE 5

3% Ag On 0.3% Ru Catalyst

| Parameter | Run 1 | Run 2 |
|---|---|---|
| HOS | 24 | 26 |
| Avg. Bed Temp., °C. | 166.7 | 181.1 |
| $O_2$, ppm | 2.9 | 2.4 |
| $C_2H_6$, mol % | 0.535 | 1.14 |
| $C_2H_4$, mol % | 46 | 46.3 |
| $C_2H_2$, mol % | <0.0001 | <0.0001 |
| $C_3H_8$, mol % | 0.032 | 0.047 |
| $C_3H_6$, mol % | 5.8 | 5.8 |
| Propadiene, mol % | 0.006 | 0.000 |
| Methylacetylene, mol % | 0.002 | 0.000 |

Example 4

Contiguous Bed of 6% Ag Loaded Catalyst/0.15% Ru Loaded Catalyst

A contiguous bed of 33 ml of Catalyst 5 and 67 ml of Catalyst 1 was loaded in the reactor with Catalyst 5 (6% Ag) being adjacent to the reactor inlet while Catalyst 1 (0.15% Ru) was loaded adjacent to the reactor outlet. The test was run at the same conditions as the single Ru catalyst bed in Example 1. The contiguous bed of Ag and Ru loaded catalysts cleaned up both oxygen and acetylene at a lower temperature with less $C_2H_6$ at the outlet than the Ru catalyst alone. The data is summarized in Table 6.

TABLE 6

Contiguous Bed of 6% Ag Catalyst On 0.15% Ru Catalyst

| Parameter | Run 1 | Run 2 | Run 3 | Run 4 |
|---|---|---|---|---|
| HOS | 24 | 48.5 | 65 | 68 |
| Avg. Bed Temp., °C. | 150 | 163 | 163 | 166 |
| $H_2$, mol % | 16.5 | — | 16.7 | — |
| CO, mol % | 0.25 | — | 0.25 | — |
| $O_2$, ppm | 0.42 | 0.04 | 0.06 | 0.005 |
| $NO_x$, ppm | <0.01 | <0.01 | <0.01 | <0.01 |
| $C_2H_6$, mol % | 0.210 | 0.374 | 0.342 | 0.370 |
| $C_2H_4$, mol % | 44.3 | 43.1 | 46.3 | 44.4 |
| $C_2H_2$, mol % | 0.0060 | <0.0001 | 0.0020 | <0.0001 |
| $C_3H_8$, mol % | 0.019 | 0.022 | 0.024 | 0.022 |
| $C_3H_6$, mol % | 5.3 | 5.1 | 5.6 | 5.3 |
| Propadiene, mol % | 0.02 | 0.02 | | |
| Methylacetylene, mol % | 0.006 | 0.002 | 0.003 | 0.002 |

Example 5

Contiguous Bed of 1% Ag Catalyst on 0.15% Ru

A contiguous bed comprised of 33 ml of Catalyst 3 and 67 ml of Catalyst 1 was loaded in reactor with Catalyst 3 being on top, closest to the reactor inlet, Catalyst 1 at the bottom, closest to the reactor outlet, to replace the 100 ml single Ru catalyst bed. The test was conducted at 1.7 MPa and 1000 GHSV. Feed B was utilized in Example 5. The catalyst bed temperature was started at about 130° C. and increased until $O_2$ at the reactor outlet was below 1 ppm, $NO_x$ was no longer detectable (<0.02 ppm), and $C_2H_2$ was no longer detectable (<1 ppm). The data obtained is summarized in Table 7.

TABLE 7

1% Ag catalyst/0.15% Ru catalyst integrated bed

| Parameter | Run 1 | Run 2 | Run 3 | Run 4 |
|---|---|---|---|---|
| HOS | 25.5 | 26.5 | 30 | 48.5 |
| Avg. Bed Temp., °C. | 156 | 166 | 164 | 171 |
| $O_2$, ppm | 0.47 | 0.08 | 0.03 | 0.05 |
| $NO_x$, ppm | <1 | <1 | <1 | <1 |
| $C_2H_2$, ppm | 177 | <1 | 46 | <1 |
| $C_2H_4$, mol % | 44.8 | 45.2 | 47.9 | 44.5 |
| $C_2H_6$, mol % | 0.177 | 0.333 | 0.271 | 0.356 |
| $C_3H_6$, mol % | 6.2 | 6.3 | 6.1 | 6.3 |
| $C_3H_8$, mol % | 0.026 | 0.031 | 0.024 | 0.032 |
| $C_2H_2$ Conv., % | 89.3 | 100 | 97.2 | 100 |
| Propadiene, mol % | 0.014 | 0.010 | 0.004 | 0.000 |
| Methylacetylene, mol % | 0.005 | 0.000 | 0.001 | 0.000 |
| Methylacetylene Conv., % | 78.7 | 100 | 94.9 | 100 |
| Propadiene Conv., % | 30.3 | 48.7 | 82.1 | 47.7 |

$NO_x$ was removed before clean-up of $O_2$ (<1 ppm) at 156° C. However, $C_2H_2$ cleanup required a higher temperature, around 170° C. At 171° C., outlet acetylene and $NO_x$ were below detectable levels and oxygen was 0.05 ppm. At clean-up conditions the ethane in the product was below 0.4 mol %.

Example 6

Varying Ratios of 1% Ag Catalyst and 0.15% Ru Catalyst in a Contiguous Bed

Catalyst 3 was loaded in front of Catalyst 1 at different volume ratios while keeping the total catalyst volume at 100 ml. The tests conditions from Example 5 were utilized with Feed C, which was similar to that used in Example 5. The optimal loading ratio range was determined to be from 15% to 55% of Ag catalyst on top of Ru catalyst. The temperature range of operation is from 160 to 185° C. at an overall GHSV of 1000.

TABLE 9

1% Ag Catalyst to 0.15% Ru Catalyst Ratio

| Parameter | Run 1 | Run 2 | Run 3 | Run 4 |
|---|---|---|---|---|
| Catalyst 3, ml | 5 | 14 | 54 | 75 |
| Catalyst 1, ml | 95 | 86 | 46 | 25 |
| HOS | 51 | 50 | 51 | 55 |
| Avg. Bed Temp., ° C. | 165.6 | 159.0 | 184.4 | 204 |
| $O_2$, ppm | 0.03 | 0.04 | 0.03 | 0.03 |
| $NO_x$, ppm | <1 | <1 | <1 | <1 |
| $C_2H_2$, ppm | <1 | <1 | <1 | <1 |
| $C_2H_4$, mol % | 41 | 43 | 38 | 41 |
| $C_2H_6$, mol % | 0.68 | 0.49 | 0.58 | 0.52 |
| $C_3H_6$, mol % | 5.03 | 5.11 | 5.62 | 5.17 |
| $C_3H_8$, mol % | 0.031 | 0.027 | 0.031 | 0.026 |
| Methylacetylene mol % | 0.0016 | 0.0005 | 0.0006 | 0.0007 |
| Propadiene, mol % | 0.0080 | 0.0081 | 0.0052 | 0.0033 |

Thus acetylenes, $NO_x$, dienes, and $O_2$ can be removed from an ethylene-containing gas stream with a minimal loss of ethylene, by contacting an ethylene-containing feedstream which further comprises $H_2$, CO, $O_2$, acetylene, dienes, and $NO_x$ with a supported silver catalyst followed by subsequent contact with a supported ruthenium catalyst, wherein the supported silver catalyst has a silver content between 0.5% by mass to 10% by mass and wherein the supported ruthenium catalyst has a ruthenium content between 0.01% by mass to 5% by mass ruthenium, in a continuous flow reactor with the catalyst held at a temperature of at least about 120° C.

It is understood that one skilled in the art may make alterations to the embodiments shown and described herein without departing from the scope of the invention. For example, it is anticipated that the reactor pressure and the gas hourly flow rate may be adjusted by those skilled in the art to accommodate different sized reactors.

What is claimed is:

1. A method for the purification of an ethylene-containing gas stream which contains acetylenes, dienes, oxygen, and nitric oxide, the method comprising at least the steps of:
   a. contacting said ethylene-containing gas stream with a supported silver catalyst having a silver content of between about 0.5 and 10% by mass to produce a first processed ethylene-containing gas stream; and
   b. contacting said first processed ethylene-containing gas stream with a supported ruthenium catalyst having a ruthenium content of between about 0.01 and 5% by mass to produce a second processed ethylene-containing gas stream containing less than about 1 ppm acetylene, less than about 1 ppm $NO_x$, and less than about 1 ppm $O_2$ with an ethylene loss of less than 2% relative to inlet ethylene.

2. The method of claim 1, wherein a catalyst support for each supported catalyst is a metal oxide selected from the group consisting of $Al_2O_3$, $SiO_2$, alumino-silicates, $TiO_2$, $ZrO_2$, ZnO, MgO, $Fe_2O_3$ and $CeO_2$ or mixtures thereof.

3. The method of claim 2, wherein said catalyst support has a BET surface area of 3 $m^2/g$ to 200 $m^2/g$ and a Hg intrusion pore volume of 0.2 ml/g to 0.8 ml/g.

4. The method of claim 1, wherein said supported silver catalyst is contained within a first reactor and said supported ruthenium catalyst is contained within a second reactor.

5. The method of claim 4, wherein said first reactor and said second reactor are continuous flow reactors.

6. The method of claim 5, wherein said ethylene-containing gas stream is contacted with said supported silver catalyst and said supported ruthenium catalyst at a temperature between about 120° C. to 250° C.

7. The method of claim 6, wherein said reactor system is operated between about 500 GHSV to 10000 GHSV based on total volume of the two catalysts.

8. The method of claim 7, wherein said ethylene-containing gas stream is contacted with said supported silver catalyst and said supported ruthenium catalyst at a pressure of between about 0.5 to 5 MPa.

9. The method of claim 8, wherein said ethylene-containing gas stream is contacted with said supported silver catalyst and said supported ruthenium catalyst at a partial pressure of hydrogen of between about 0.05 MPa and 2 MPa.

10. The method of claim 1, wherein a quantity of said supported silver catalyst is between about 1% to 99% by volume of a total combined volume of said supported silver catalyst and said supported ruthenium catalyst contacting said ethylene-containing gas stream.

11. The method of claim 10, wherein the quantity of said supported silver catalyst is between about 5% to 75% by volume of the total combined volume of said supported silver catalyst and said supported ruthenium catalyst contacting said ethylene-containing gas stream.

* * * * *